United States Patent
Imamura

(10) Patent No.: US 12,163,846 B2
(45) Date of Patent: Dec. 10, 2024

(54) STICKING-TYPE DEVICE FOR LIVING BODY

(71) Applicant: Murata Manufacturing Co., Ltd., Nagaokakyo (JP)

(72) Inventor: Yuuichi Imamura, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 982 days.

(21) Appl. No.: 17/108,050

(22) Filed: Dec. 1, 2020

(65) Prior Publication Data

US 2021/0076945 A1     Mar. 18, 2021

Related U.S. Application Data

(63) Continuation of application No. PCT/JP2019/020818, filed on May 27, 2019.

(30) Foreign Application Priority Data

Jun. 6, 2018    (JP) ................................. 2018-108589

(51) Int. Cl.
    *G01K 13/20*          (2021.01)
    *A61B 5/00*           (2006.01)
    (Continued)

(52) U.S. Cl.
    CPC ............ *G01K 13/20* (2021.01); *A61B 5/7475* (2013.01); *G01K 1/14* (2013.01); *H01H 13/14* (2013.01)

(58) Field of Classification Search
    CPC .......... G01K 13/20; G01K 1/14; G01K 1/143; H01H 13/14
    See application file for complete search history.

(56) References Cited

U.S. PATENT DOCUMENTS

2012/0238901 A1*   9/2012   Augustine ................ A61B 5/01
                                                           600/549
2016/0045135 A1*   2/2016   Kim ...................... A61B 5/4812
                                                           600/391

(Continued)

FOREIGN PATENT DOCUMENTS

CN         103997994 A    *   8/2014         ......... A61B 5/02208
JP          S6117034 A       1/1986
(Continued)

OTHER PUBLICATIONS

Translation of KR20100012871U.*

(Continued)

*Primary Examiner* — Mirellys Jagan
(74) *Attorney, Agent, or Firm* — ArentFox Schiff LLP

(57) ABSTRACT

A deep body thermometer includes an upper exterior body including a foamed material of closed cells or semi-closed cells having waterproof properties and that is in a substantially hat-like shape in a side view, a lower exterior body having a peripheral edge in close contact with the upper exterior body, a sticking member that has adhesiveness and one surface that is stuck to an outer side surface of the lower exterior body, a wiring substrate housed in an accommodation space defined by the upper and exterior bodies, and an operation switch electrically connected to the wiring substrate. The operation switch receives an operation input in which an input direction of operation force is substantially parallel to the sticking member and does not receive an operation input in which an input direction of operation force is substantially perpendicular to the sticking member.

20 Claims, 11 Drawing Sheets

(51) Int. Cl.
*G01K 1/14* (2021.01)
*H01H 13/14* (2006.01)

(56) References Cited

U.S. PATENT DOCUMENTS

| | | | |
|---|---|---|---|
| 2017/0150927 A1* | 6/2017 | Kubota | A61B 5/029 |
| 2018/0028072 A1* | 2/2018 | Shi | A61B 5/6833 |
| 2018/0188114 A1* | 7/2018 | Ou Yang | G01J 5/041 |
| 2018/0235502 A1 | 8/2018 | Nishimura et al. | |
| 2019/0350531 A1* | 11/2019 | Shimuta | A61B 5/6833 |

FOREIGN PATENT DOCUMENTS

| | | |
|---|---|---|
| JP | 2002143098 A | 5/2002 |
| JP | 2007195618 A | 8/2007 |
| JP | 2009190534 A | 8/2009 |
| JP | 2010223743 A | 10/2010 |
| JP | 201687209 A | 5/2016 |
| JP | 2016214731 A | 12/2016 |
| JP | 2017217255 A | 12/2017 |
| JP | 6628919 B1 * | 1/2020 |
| KR | 102010131070 A | 12/2010 |
| KR | 2020100012871 U | 12/2010 |
| KR | 101846780 B1 | 4/2018 |
| WO | 2017043595 A1 | 3/2017 |
| WO | 2017108215 A1 | 6/2017 |

OTHER PUBLICATIONS

International Search Report Issued for PCT/JP2019/020818, date of mailing Jul. 30, 2019.
Written Opinion of the International Searching Authority issued for PCT/JP2019/020818, date of mailing Jul. 30, 2019.
Japanese Office Action issued for corresponding Japanese Patent Application No. 2020-523643, Japanese Office Action dated Oct. 12, 2021.

* cited by examiner

STICKING-TYPE DEVICE FOR LIVING BODY

CROSS REFERENCE TO RELATED APPLICATIONS

The present application is a continuation of PCT/JP2019/020818 filed May 27, 2019, which claims priority to Japanese Patent Application No. 2018-108589, filed Jun. 6, 2018, the entire contents of each of which are incorporated herein by reference.

TECHNICAL FIELD

The present invention relates to a sticking-type device for a living body.

BACKGROUND

A current thermometer exists that has been proposed to be stuck to a body surface and continuously measures a body temperature to acquire body temperature data. For example, Patent Document 1 (identified below) discloses a sticking-type thermometer for continuous measurement that is stuck to a body surface of a subject and measures a deep body temperature of the subject.

More specifically, the sticking-type thermometer can be stuck to a body surface of a subject, and has a battery built-in type IC tag having a temperature sensor, a power supply switch for turning on the battery built-in type IC tag, and a holding unit for holding the power supply switch in an ON state. Further, the battery built-in type IC tag has a configuration in which an antenna and a processing unit are sandwiched and fixed between a front surface film and a back surface film.

Patent Document 1: Japanese Unexamined Patent Application Publication No. 2010-223743.

In the sticking-type thermometer described in Patent Document 1, a push-type power supply switch (e.g., an operation switch) is disposed on a top surface of the thermometer. For this reason, in a case where the sticking-type thermometer is stuck to the body surface, the power supply switch protrudes in a vertical direction from the surface of the body, so that the power supply switch may be erroneously pressed, that is, an erroneous operation may be received. For example, when the sticking-type thermometer is stuck to the chest, the power supply switch can be erroneously pressed down, for example, when lying in a prone position, when a shoulder strap of a bag comes into contact therewith, or the like. As a result, an unintended operation (e.g., a malfunction) may be caused by the user.

SUMMARY OF THE INVENTION

Accordingly, the exemplary embodiments of the present invention have been made in order to solve the above-described problems. In particular, an object of the present invention is to provide a sticking-type device for a living body, which is configured to be stuck to the living body for use and is constructed to prevent the operation switch from being erroneously operated (i.e., receiving an erroneous switch operation).

In an exemplary aspect, a sticking-type device for a living body is provided that is configured to be stuck to the living body for use. The sticking-type device includes an exterior body having an accommodation space inside the exterior body; a sticking member having adhesiveness, one surface of the sticking member being stuck to a bottom surface of the exterior body; a wiring substrate housed in an accommodation space of the exterior body; and an operation switch electrically connected to the wiring substrate and configured to receive an operation performed by a user. Moreover, the operation switch receives an operation input in which an input direction of operation force is substantially parallel to a main surface of the sticking member, and does not receive an operation input in which an input direction of operation force is substantially perpendicular to a main surface of the sticking member.

According to the sticking-type device for the living body, the operation switch receives an operation input in which an input direction of operation force is substantially parallel (i.e., from the side) with respect to the sticking member (i.e., the body surface when being stuck to the living body). By this construction, the operation switch does not receive an operation input in which an input direction of operation force is substantially perpendicular (i.e., from above) with respect to the sticking member. Therefore, even when the force in a direction substantially perpendicular to the body surface is input to the operation switch, the operation is not received. As a result, the operation switch can be prevented from being erroneously operated (i.e., receiving an erroneous switch operation) in the sticking-type device for the living body, which is stuck to the living body for use.

According to the present invention, an operation switch is configured to prevent it from being erroneously operated (i.e., receiving an erroneous switch operation) in the sticking-type device for the living body, which is stuck to the living body for use.

DETAILED DESCRIPTION OF EMBODIMENTS

Figure 1:
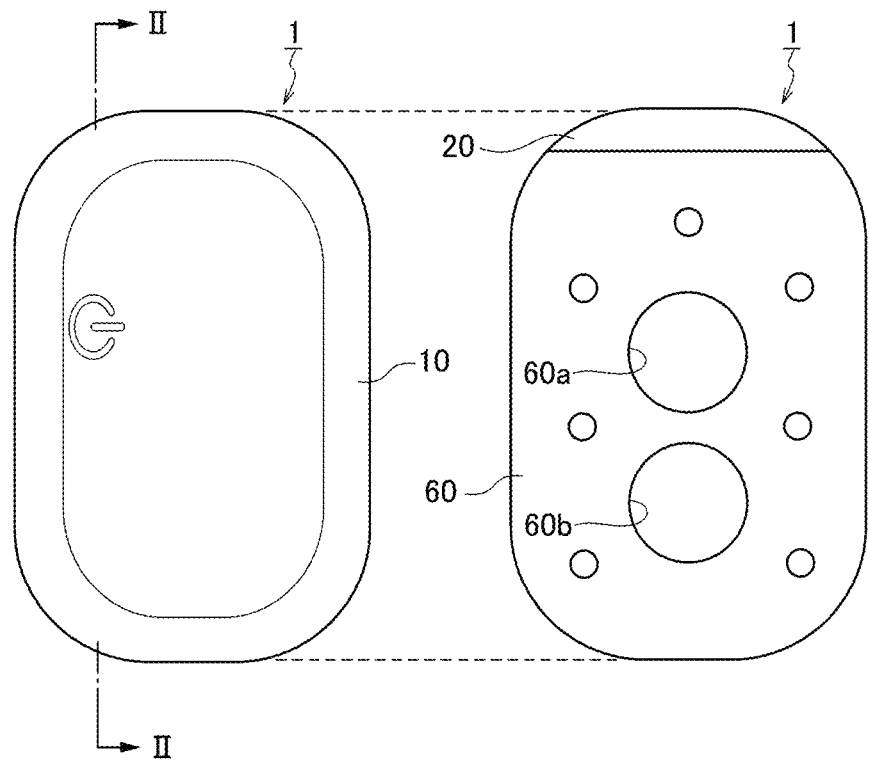
FIG. 1 includes a plan view and a bottom view illustrating an appearance of a deep body thermometer according to a first exemplary embodiment.

Hereinafter, exemplary embodiments will be described in detail with reference to the accompanying drawings. Note that, in the drawings, the same reference numerals are used to designate the same or corresponding parts. Further, in each of the drawings, the same elements are denoted by the same reference numerals, and description thereof will not be repeated. Additionally, here, a non-heating-type deep body thermometer (hereinafter simply referred to as a "deep body thermometer") will be described as an example of a sticking-type device for a living body according to the exemplary embodiments of the present invention.

First Exemplary Embodiment

Figure 2:
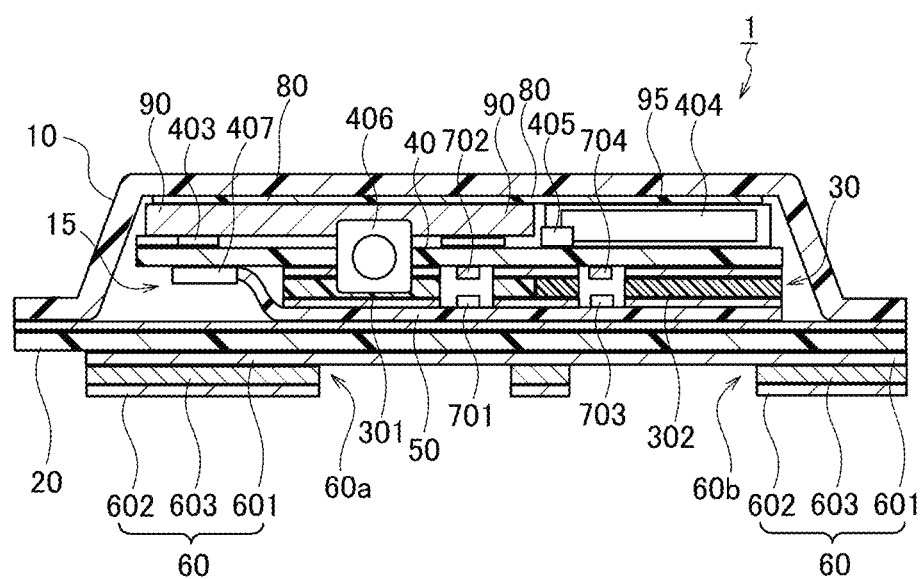
FIG. 2 is a cross-sectional view illustrating a configuration of the deep body thermometer according to the first exemplary embodiment.
Figure 3:
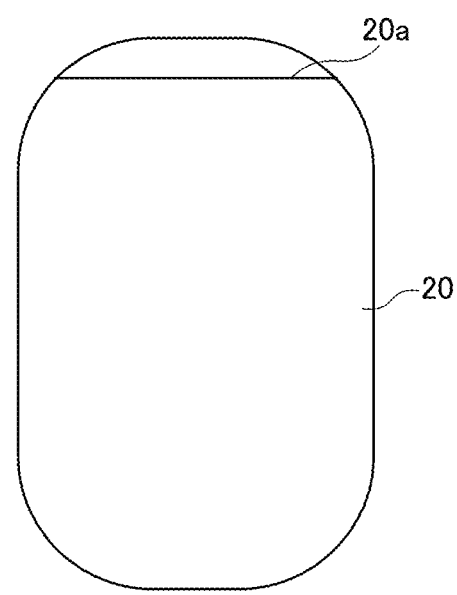
FIG. 3 is a plan view illustrating a lower exterior body configuring the deep body thermometer according to the first exemplary embodiment.
Figure 4:
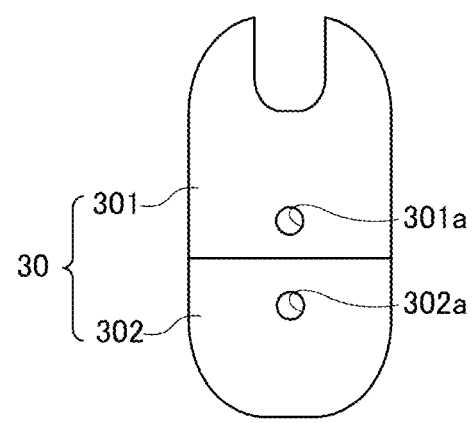
FIG. 4 is a plan view illustrating a thermal resistor layer configuring the deep body thermometer according to the first exemplary embodiment.
Figure 5:
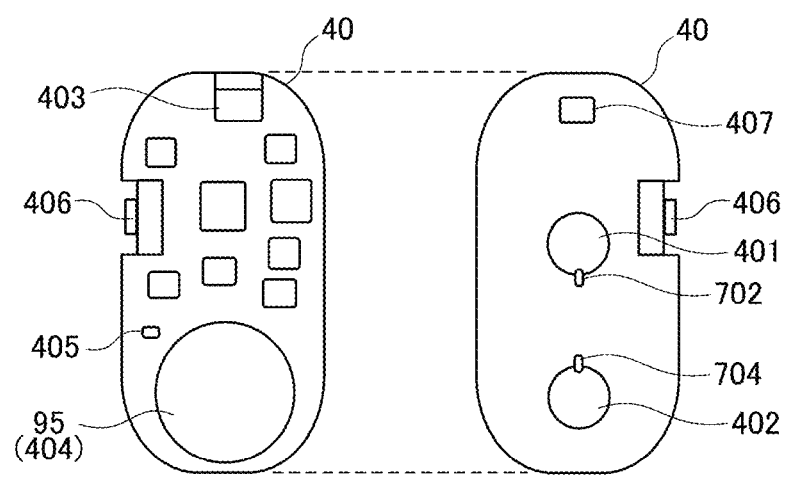
FIG. 5 includes a plan view and a bottom view illustrating a wiring substrate configuring the deep body thermometer according to the first exemplary embodiment.
Figure 6:
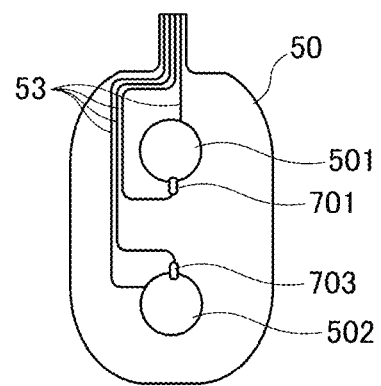
FIG. 6 is a plan view illustrating a flexible substrate configuring the deep body thermometer according to the first exemplary embodiment.
Figure 7:
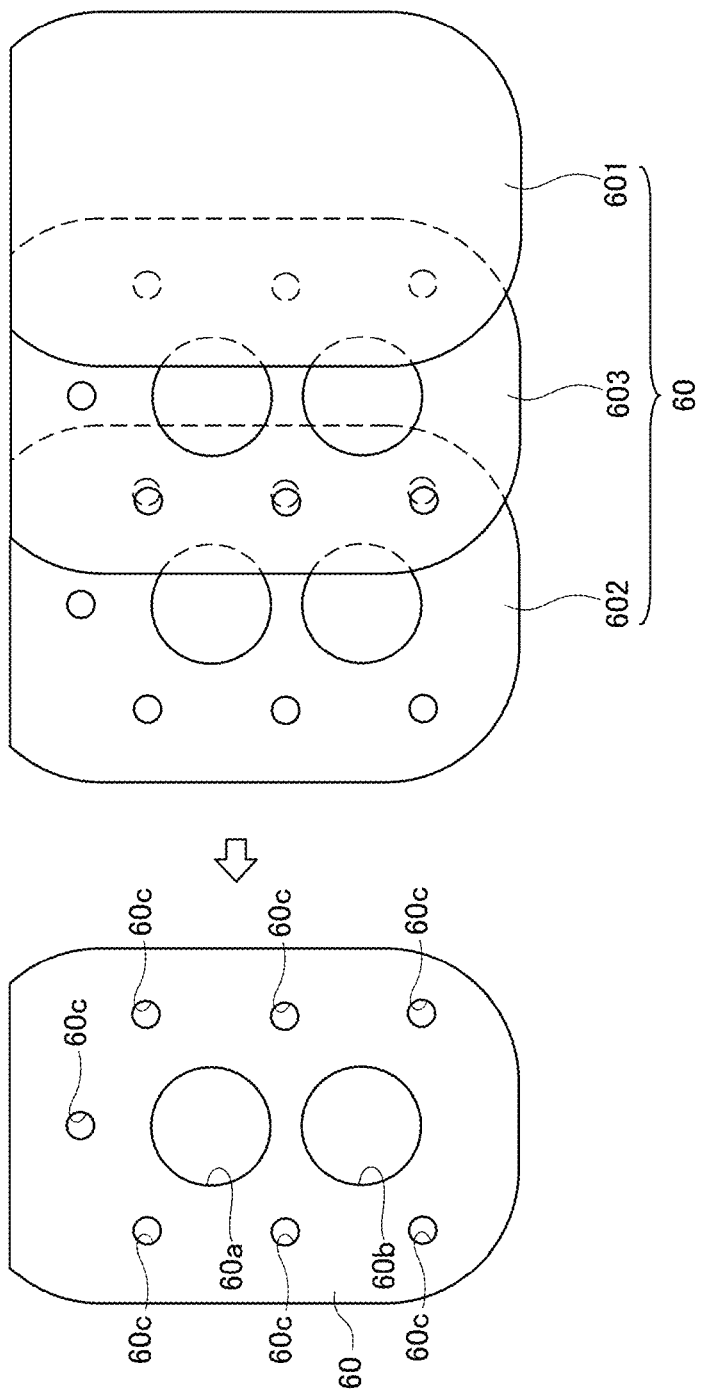
FIG. 7 includes a plan view and an exploded view illustrating a sticking member configuring the deep body thermometer according to the first exemplary embodiment.

First, a configuration of a deep body thermometer 1 according to a first exemplary embodiment will be described with reference to FIG. 1 to FIG. 7. FIG. 1 includes a plan view and a bottom view illustrating an appearance of the deep body thermometer 1. FIG. 2 is a cross-sectional view (i.e., a cross-sectional view taken along a line II-II in FIG. 1) illustrating the configuration of the deep body thermometer 1. FIG. 3 is a plan view illustrating a lower exterior body 20 configuring the deep body thermometer 1. FIG. 4 is a plan view illustrating a thermal resistor layer 30 configuring the deep body thermometer 1. FIG. 5 includes a plan view and a bottom view illustrating a wiring substrate 40 configuring the deep body thermometer 1. FIG. 6 is a plan view illustrating a flexible substrate 50 configuring the deep body thermometer 1. FIG. 7 includes a plan view and an exploded view illustrating a sticking member 60, which has adhesiveness, configuring the deep body thermometer 1.

The deep body thermometer 1 is a non-heating type deep body thermometer that obtains a heat flow rate from a deep body of a user (e.g., a patient or a subject) based on a difference between temperatures detected by a first temperature sensor 701 and a second temperature sensor 702 and a difference between temperatures detected by a third temperature sensor 703 and a fourth temperature sensor 704, and acquires a deep body temperature. Further, the deep body thermometer 1 is a sticking-type (e.g., a patch-type) deep body thermometer which is stuck to a body surface of the user and continuously measures the body temperature to acquire body temperature data. In particular, the deep body thermometer 1 is a deep body thermometer constructed to prevent an operation switch 406 from being erroneously operated (i.e., receiving an erroneous switch operation).

The deep body thermometer 1 is configured to mainly include an upper exterior body 10, the lower exterior body 20, a body temperature measuring unit 15, a lining member 80, a buffer member 90, and the sticking member 60. Further, the body temperature measuring unit 15 is configured to mainly include the thermal resistor layer 30, the wiring substrate 40 on which the second temperature sensor 702 and the fourth temperature sensor 704 are mounted, and the flexible substrate 50 on which the first temperature sensor 701 and the third temperature sensor 703 are mounted. Hereinafter, each of the elements of the deep body thermometer 1 will be described in detail.

The upper exterior body 10 is made of, for example, a foamed material of closed cells or semi-closed cells having waterproof properties and heat retaining properties. In order to prevent the temperature of the body temperature measuring unit 15 from being locally changed due to a sudden variation (e.g., a change) in an outside air temperature, it is preferable to use a foamed material having low thermal conductivity for the upper exterior body 10. Note that, as the material, for example, polyurethane, polystyrene, polyolefin, or the like is preferably used. Further, as a processing method of the upper exterior body 10, for example, vacuum molding is preferably used. The upper exterior body 10 is formed to have a substantially hat-shaped cross section so as to house the body temperature measuring unit 15 (e.g., the thermal resistor layer 30, the wiring substrate 40, the flexible substrate 50, and the like). Therefore, a side surface of the thermal resistor layer 30 is covered with the foamed material, and the side surface of the thermal resistor layer 30 is prevented from being exposed to the outside air.

The lower exterior body 20 is formed of, for example, a non-foamed resin film having waterproof properties (e.g., a low moisture permeability) and higher thermal conductivity than that of the upper exterior body 10. Examples of the material include polypropylene, polyethylene, polyester, polyimide, and the like, and polyethylene terephthalate (PET) is particularly preferably used. The lower exterior body 20 is formed in a planar shape (flat) such that the flexible substrate 50 (e.g., body temperature measuring unit 15) to which the first temperature sensor 701 and the third temperature sensor 703 are attached can be fixed thereto in a close contact manner. Note that, since a gap between the body temperature measuring unit 15 and the lower exterior unit 20 causes thermal resistance to vary and this influences heat fluxes, it is preferable that the body temperature measuring unit 15 and the lower exterior body 20 be fixed in a close contact manner by a method of sticking with a double-sided adhesive tape, a method of fixing with an adhesive, or the like. The upper exterior body 10 and the lower exterior body 20 are formed to have the same (or substantially the same) sizes (outer dimensions), and are formed to have sizes of, for example, about 40 to 100 (mm) in a longitudinal direction and about 20 to 60 (mm) in a lateral direction.

Then, a peripheral edge portion of the upper exterior body 10 having the substantially hat-shaped cross section and a peripheral edge portion of the lower exterior body 20 formed in a planar shape are fixed in a close contact manner by, for example, sticking with a double-sided adhesive tape, fixing with an adhesive, heat sealing, or the like. Note that, in order to achieve waterproof performance, it is desirable that a portion where the upper exterior body 10 and the lower exterior body 20 are fixed in the close contact manner be flat and have structure in which wrinkles are less likely to be formed. That is, it is preferable that an outer edge portion of the lower exterior body 20 be flat, an outer edge portion of the opposing upper exterior body 10 be also flat, and they be stuck and fixed to each other in a close contact manner. In this case, since force is uniformly applied to the portion where the upper exterior body 10 and the lower exterior body 20 are fixed in a close contact configuration, problems, such as generation of wrinkles, that adversely affect the waterproof performance can be minimized or eliminated.

As illustrated in FIG. 2, the body temperature measuring unit 15 is configured by laminating the flexible substrate 50, the thermal resistor layer 30, and the wiring substrate 40 in this order from the lower exterior body 20 side.

The thermal resistor layer 30 includes two thermal resistors having different thermal resistance values, that is, a first thermal resistor 301 and a second thermal resistor 302 in order to form two heat fluxes (see, e.g., FIG. 4). As the first thermal resistor 301, a material having higher thermal conductivity (i.e., a lower thermal resistance value) than that of the second thermal resistor 302, for example, plastics such as polypropylene, polyethylene, acrylic, polycarbonate, epoxy resin, and the like are preferably used. As the second thermal resistor 302, a material having lower thermal conductivity (i.e., a higher thermal resistance value) than that of the first thermal resistor 301, for example, foamed plastic (e.g., foamed material) such as polyurethane, polystyrene, polyolefin, or the like is preferably used. However, plastic, rubber, or the like which is not foamed may also be used. Note that, here, the thermal conductivity of the metal such as copper, aluminum, or the like is equal to or more than 100 [W/m/K], whereas the thermal conductivity of the plastic such as polypropylene, polyethylene, acrylic, polycarbonate, epoxy resin, or the like is about 0.1 to 0.5 [W/m/K], and is lower by about three digits. The thermal conductivity of the foamed plastic is much lower than that by almost one digit. The thermal conductivity of the air is much lower and is 0.024 [W/m/K]. The first thermal resistor 301 and the second thermal resistor 302 are formed to have substantially the same thickness in order to reduce cost by enabling the wiring substrate 40 and the flexible substrate 50 to be laminated on each other.

A first through-hole 301*a* penetrating in a thickness direction is formed in the first thermal resistor 301 configuring the thermal resistor layer 30. Similarly, a second through-hole 302*a* penetrating in a thickness direction is formed in the second thermal resistor 302 configuring the thermal resistor layer 30. The first through-hole 301*a* is formed such that the first temperature sensor 701 and the second temperature sensor 702 are housed in an inner side portion thereof in a plan view. In other words, the first temperature sensor 701 and the second temperature sensor 702 which are paired are arranged inside (e.g., in the inner side portion of) the first through-hole 301*a* along the thickness direction of the first thermal resistor 301. Similarly, the second through-hole 302*a* is formed such that the third temperature sensor 703 and the fourth temperature sensor 704 are housed in an inner side portion thereof in a plan view. In other words, the third temperature sensor 703 and the fourth temperature sensor 704 which are paired are arranged inside (e.g., in the inner side portion of) the second through-hole 302*a* along the thickness direction of the second thermal resistor 302.

Here, as the first temperature sensor 701 to the fourth temperature sensor 704 (hereinafter, also collectively referred to as "temperature sensors (corresponding to a biological sensor 70"), for example, thermistors, temperature measuring resistors, or the like whose resistance values vary depending on temperatures which are biological signals are preferably used. Note that, it is preferable that the temperature sensors 70 have small heat capacitance as much as possible from the viewpoint of enhancing responsiveness. Therefore, for example, chip thermistors are preferably used as the temperature sensors 70. Each of the first temperature sensor 701 to the fourth temperature sensor 704 is electrically connected to a processing circuit (MCU), which will be described later, via a printed wiring, and electric signals corresponding to the temperature are read by the processing circuit (MCU).

In order to reduce the size of the thermal flow-type deep body thermometer 1, it is important to make the thermal resistor layer 30 (e.g., the first thermal resistor 301 and the second thermal resistor 302) small, however, when the thermal resistor layer 30 is made to be small, differences in an output value between the paired temperature sensors 70 become small, and thus, measurement errors may therefore be increased. Here, since the temperature sensors 70 (e.g., chip thermistor) have a substantially rectangular parallelepiped shape and have a thickness, the thickness of the temperature sensors 70 cannot be ignored when the thermal resistor layer 30 is made to be thin. When the temperature sensors 70 are in contact with the side surface of the thermal resistor layer 30, heat is transferred thereto from the contact portion, and therefore, the temperatures (e.g., detected values) of the temperature sensors 70 may become temperature values deviating from the surface temperature of the thermal resistor layer 30. As such and in order to reduce this influence, structure is provided in which the through-holes 301*a* and 302*a* are formed in the thermal resistor layer 30 around the temperature sensors 70, such that the temperature sensors 70 do not make contact with the side surface of the thermal resistor layer 30.

The wiring substrate 40 is, for example, a rigid substrate such as a glass epoxy substrate. On the wiring substrate 40, there is mounted the processing circuit for processing an output signal of each of the first temperature sensor 701 to the fourth temperature sensor 704 to acquire deep body temperature data. In addition, a wireless communication unit 403 which transmits (e.g., outputs) the acquired deep body temperature data and a coin battery 404 which supplies power to the processing circuit and the wireless communication unit 403 are mounted on the wiring substrate 40. The processing circuit mainly includes a temperature input circuit and an arithmetic processing circuit. The temperature input circuit is configured to include, for example, an amplifier (for example, an operational amplifier), an analog/digital converter (an A/D converter), and the like for reading the detection signals (output voltages) of the temperature sensors 70. The temperature input circuit amplifies analog signals output from the temperature sensors 70, converts the analog signals into digital signals, and outputs the digital signals to the arithmetic processing circuit.

The arithmetic processing circuit is configured to calculate the deep body temperature from the read measurement data (e.g., temperature values). In an exemplary aspect, the arithmetic processing circuit includes, for example, an MCU (Micro Control Unit), an EEPROM, a RAM, and the like, and calculates the deep body temperature based on the detected values of the temperature sensors 70, which have been read via the temperature input circuit. In addition, the arithmetic processing circuit stores the calculated deep body temperature data in a memory such as the RAM. Further, the arithmetic processing circuit outputs the calculated deep body temperature data to the wireless communication unit 403 to thereby output (e.g., transmit) the calculated deep body temperature data to an external device wirelessly.

Note that, here, the arithmetic processing circuit calculates (e.g., estimates) the deep body temperature based on the temperature difference between the front and back surfaces of the thermal resistors 301 and 302, which is caused by the difference between the two heat fluxes formed using the two thermal resistors 301 and 302 having different thermal resistances. More specifically, the arithmetic processing circuit calculates a deep body temperature Tb based on the following equation (1), for example:

$$Tb=\{T1\cdot(T3-T4)*Ra1-T3\cdot(T1-T2)*Ra2\}/\{(T3-T4)*Ra1-(T1-T2)*Ra2\} \quad (1)$$

Note that Tb represents a deep body temperature, T1 represents a temperature detected by the first temperature sensor 701, T2 represents a temperature detected by the second temperature sensor 702, and Ra1 represents a thermal resistance value of the first thermal resistor 301. In addition, T3 represents a temperature detected by the third temperature sensor 703, T4 represents a temperature detected by the fourth temperature sensor 704, and Ra2 represents a thermal resistance value of the second thermal resistor 302.

Here, since Ra1 and Ra2 are known, the deep body temperature Tb can be uniquely determined by detecting the four temperatures (i.e., T1, T2, T3, T4).

On a lower surface of the wiring substrate 40, the second temperature sensor 702 which acquires the temperature of an upper surface (e.g., outside air side) of the first thermal resistor 301 and the fourth temperature sensor 704 which detects the temperature of an upper surface (e.g., outside air side) of the second thermal resistor 302 are mounted. More specifically, thermal equalization patterns 401 and 402 for equalizing peripheral temperature distribution are formed on the lower surface of the wiring substrate 40, one electrode of the second temperature sensor 702 is connected to the thermal equalization pattern 401, and one electrode of the fourth temperature sensor 704 is connected to the thermal equalization pattern 402. The thermal equalization patterns 401 and 402 are made of, for example, a material having high thermal conductivity, such as a metal film.

Further, in order to prevent the temperature of only a part of the wiring substrate 40 from being changed due to influences of the outside air temperature and the like, it is preferable to provide, on a back surface side (e.g., outside air side) of a wiring layer on which the second temperature sensor 702 and the fourth temperature sensor 704 are mounted, an equalization member (e.g., a metal film) having high thermal conductivity for thermally equalizing the influences of the temperature distribution of the outside air temperature. Here, as the equalization member, a metal foil, a metal thin plate, or the like may be used, but it is desirable to form the equalization member as a wiring pattern (e.g., solid pattern) of an inner layer of the wiring substrate 40 (e.g., multilayer rigid substrate), similarly to the wiring layer formed on the wiring substrate 40. In this case, the wiring pattern (e.g., solid pattern) of the inner layer, which is used as the equalization member, can be a ground pattern but is preferably an independent pattern that is connected to no electric circuit and through which no current flows.

The wireless communication unit 403 transmits the acquired deep body temperature data (e.g., biological information) to an external control device or an information terminal (for example, a smart phone or the like). Here, the wireless communication unit 403 transmits the deep body temperature data to the external control device or the information terminal using, for example, Bluetooth® or the like. The thin coin battery 404 supplies electric power to the processing circuit (i.e., an electronic component), the wireless communication unit 403, and the like described above. The coin battery 404 is housed in a battery holder 95 mounted on or otherwise attached to the wiring substrate 40. The battery holder 95 is disposed between the wiring substrate 40 and the lining member 80. That is, the battery holder 95 also serves as a spacer member supporting the lining member 80. Note that, in order to reduce a flat area (e.g., a sticking area) of the body temperature measuring unit 15 (i.e., deep body thermometer 1) and to prevent influences of heat generation caused by change in the outside air temperature and operations of the wireless communication unit 403 from occurring, the wireless communication unit 403 and the coin battery 404 (battery holder 95) are disposed on the opposite side (e.g., upper surface side) to the temperature sensors 70 with the wiring substrate 40 interposed therebetween.

The operation switch 406 (hereinafter also referred to as a "power supply switch") which receives an ON/OFF operation or the like of a power supply by the user with the upper exterior body 10 interposed therebetween is electrically connected to the wiring substrate 40 (processing circuit). A notch portion is formed in a side portion of the wiring substrate 40, and the power supply switch 406 is attached so as to be housed in the notch portion, in a manner such that a main surface of the wiring substrate 40 and an operation direction of the power supply switch 406 are substantially parallel to each other. The wiring substrate 40 is housed in an accommodation space defined by the upper exterior body 10 and the lower exterior body 20 in a manner such that the power supply switch 406 faces the back surface (i.e., rear surface) of a side surface portion of the upper exterior body 10. That is, the power supply switch 406 is arranged on the side surface of the upper exterior body 10. Therefore, the power supply switch 406 receives an operation input in which an input direction of operation force is substantially parallel (i.e., from the side of the upper exterior body 10) with respect to the wiring substrate 40 and the sticking member 60 (i.e., the body surface when the deep body thermometer 1 is stuck to the living body). Based on this configuration, the power supply switch 406 is prevented from receiving an operation input in which an input direction of operation force is substantially perpendicular (i.e., from above) with respect to the wiring substrate 40 and the sticking member 60.

As the power supply switch 406, for example, a push button switch, a rocker switch, or the like is preferably used. Note that in a case of the push button switch, a push button switch employing an alternate operation of holding an ON state even when a fingertip is separated therefrom is preferably used. Further, the power supply switch 406 is preferably a surface mount type, but a lead type may also be used.

Here, in order to prevent the power supply switch 406 from being erroneously (e.g., accidentally) pressed to turn ON/OFF the power supply and prevent the power supply switch 406 from pushing up the upper exterior body 10, the power supply switch 406 is disposed inside (in the accommodation space of) the upper exterior body 10 so as not to make contact with the back surface of the side surface portion of the upper exterior body 10. To be more specific, a gap between a button top surface of the power supply switch 406 and the back surface (i.e., rear surface) of the side surface portion of the upper exterior body 10 is preferably set to a range of, for example, 0 to 4 (mm), and more preferably set to a range of 0.5 to 1.5 (mm). In addition, a stroke of the power supply switch 406 is preferably set to a range of 0.1 to 1 (mm), and more preferably set to a range of 0.1 to 0.3 (mm), for example.

Further, on the upper surface of the wiring substrate 40, an LED 405 which lights or flickers in accordance with a user's operation and a body temperature measurement state (for example, ON/OFF of the power supply switch 406, start/end of measurement, and the like) is preferably mounted. Note that instead of the LED, for example, a VCSEL or the like may be used. Further, an FPC connector 407 for electrically connecting the flexible substrate 50 is attached to the lower surface side of the wiring substrate 40.

The flexible substrate (FPC) 50 is made of, for example, polyimide, polyester (PET), or the like and has flexibility. On the flexible substrate 50, the first temperature sensor 701 which acquires the temperature of the first thermal resistor 301 on a skin side and the third temperature sensor 703 which acquires the temperature of the second thermal resistor 302 on a skin side are mounted. More specifically, as illustrated in FIG. 6, in order to equalize the peripheral temperature distribution, thermal equalization patterns 501 and 502 are formed on the flexible substrate 50, one terminal of the first temperature sensor 701 is connected to the thermal equalization pattern 501, and one terminal of the third temperature sensor 703 is connected to the thermal equalization pattern 502. The thermal equalization patterns 501 and 502 are made of, for example, a material having high thermal conductivity, such as a metal film. Each of the first temperature sensor 701 and the third temperature sensor 703 is connected to the wiring substrate 40 (i.e., processing circuit) via wiring patterns 53 and the FPC connector 407, and electric signals (e.g., voltage values) corresponding to the temperatures are read by the processing circuit (e.g., temperature input circuit). Note that, as described above, the lower exterior body 20, the flexible substrate 50, the thermal resistor layer 30, and the wiring substrate 40 are fixed to each other in a close contact manner by, for example, a double-sided adhesive tape or the like so as to form no gap therebetween in order to form the heat fluxes.

The lining member 80 formed in a thin plate shape (e.g., a sheet shape) thinner than the buffer member 90, which will be described later, is disposed on the back surface (e.g., rear surface) of a top surface of the upper exterior body 10, that is, between the upper exterior body 10 and the buffer member 90 and the battery holder (e.g., spacer member) 95. The lining member 80 is made, for example, of a resin material such as PET having flexibility, so as to be capable of being curved. In order to suppress wrinkles on the upper exterior body 10, one surface of the lining member 80 is stuck to and attached to the back surface (e.g., rear surface) of the top surface of the upper exterior body 10 by, for example, a double-sided adhesive tape or the like. Note that, the lining member 80 may be made of a thin metal plate or the like. Further, in order to prevent the operation of the power supply switch 406 from being hindered, the lining member 80 may be provided with a notch in accordance with the power supply switch 406, similarly to the above-described wiring substrate 40.

Between the upper surface (i.e., main surface) of the wiring substrate 40 and the lining member 80, the buffer member 90 which has buffer properties (e.g., cushioning properties) and is formed in a plate shape is disposed. The buffer member 90 is formed to be thicker than a height (i.e., a tallness) of the electronic component from a mounting surface of the wiring substrate 40. The buffer member 90 is stuck and attached to another surface of the lining member 80 by, for example, a double-sided adhesive tape or the like.

As illustrated in FIG. 7, the sticking member 60 is configured to include a first adhesive layer 601 which is stuck to an outer side surface of the lower exterior body 20, a ventilation layer 603 (i.e., a moisture permeable layer transmitting moisture) which is stuck to the first adhesive layer 601 and has ventilation properties, and a second adhesive layer 602 which is stuck to the ventilation layer 603. Then, in a case where the deep body thermometer 1 is stuck to the skin for use, sweat accumulated between the skin and the deep body thermometer 1 (e.g., lower exterior body 20) for a long time may cause the skin to be inflamed, however, by providing the ventilation layer 603 which allows moisture to pass in the sticking member 60, stuffiness by sweat or the like is suppressed. As the ventilation layer 603 (i.e., the moisture permeable layer), for example, nonwoven fabric can be suitably used. Note that in place of the nonwoven fabric, cloth or knitted fabric may be used. Further, paper, wood, sponge/foamed material of open-cells, or the like may be used, or plastic, rubber, or metal structure having grooves or holes extending from the center of the body temperature measuring unit 15 toward a peripheral edge thereof may be used.

Since the ventilation layer 603 (i.e., the moisture permeable layer) contains the air therein, the heat conductivity thereof is usually low. Therefore, when the ventilation layer 603 is positioned between the skin and the sensors, a body temperature measurement accuracy is affected. In consideration of this (in order to stably measure the body temperature), the ventilation layer 603 is not arranged in a region overlapping with the first temperature sensor 701 and the third temperature sensor 703, which measure the temperatures of the skin, and the thermal equalization patterns 501 and 502 connected to them.

Here, a case where the nonwoven fabric is used as the ventilation layer 603 (i.e., the moisture permeable layer) will be described as an example. As illustrated in FIG. 7, double-sided adhesive tapes (the first adhesive layer 601 and the second adhesive layer 602) having biocompatibility are stuck to both sides of the nonwoven fabric (the ventilation layer 603). In the ventilation layer 603 and the second adhesive layer 602, through-holes 60a and 60b in which the first temperature sensor 701 and the third temperature sensor 703 are housed in inner side portions in a plan view are formed in a thickness direction. Here, it is preferable that no through-hole be formed in the double-sided adhesive tape (first adhesive layer 601) to be stuck to the lower exterior body 20. This is because when the through-hole is formed therein (i.e., when the first adhesive layer 601 is not present), the lower exterior body 20 does not make close contact with the skin and the measurement accuracy may possibly be lowered.

Further, in general, since the double-sided adhesive tape (second adhesive layer 602) is inferior in the moisture permeability to the nonwoven fabric (ventilation layer 603), it is preferable to form a plurality (seven in the example illustrated in FIG. 7) of through-holes 60c formed in the thickness direction in at least the second adhesive layer 602. In this case, for example, it is preferable to arrange the through-holes 60c having the diameter of about 1 to 10 mm with intervals of about 2 to 20 mm. Note that, instead of the through-holes 60c, for example, a notch having a crossing portion (i.e., a notch intersecting in a cross shape) may be formed. In this case, it is preferable to arrange the intersecting notches having the length of about 1 to 10 mm with intervals of about 2 to 20 mm.

Figure 8:
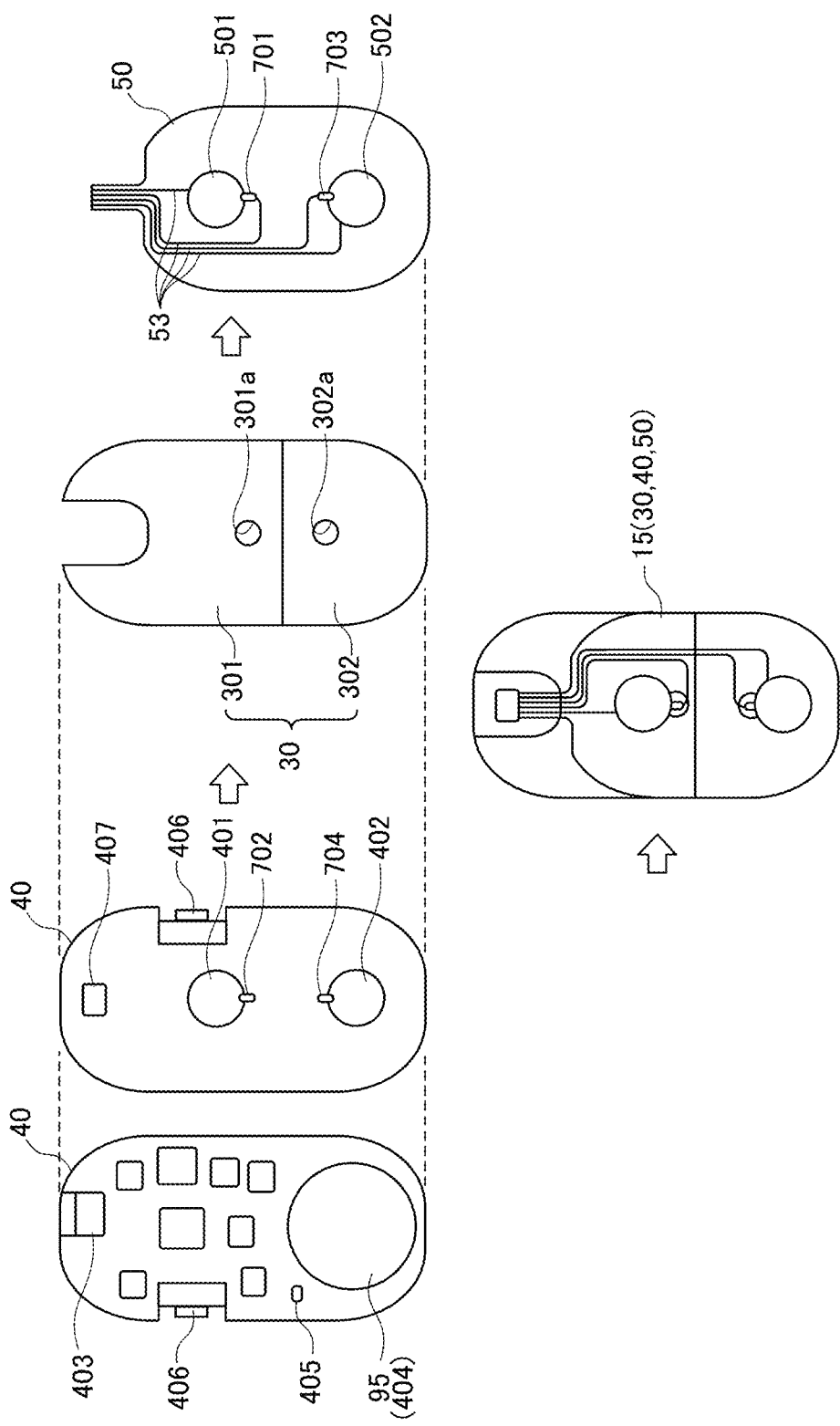
FIG. 8 is a view (part 1) for explaining a method of assembling the deep body thermometer according to the first exemplary embodiment.
Figure 9:
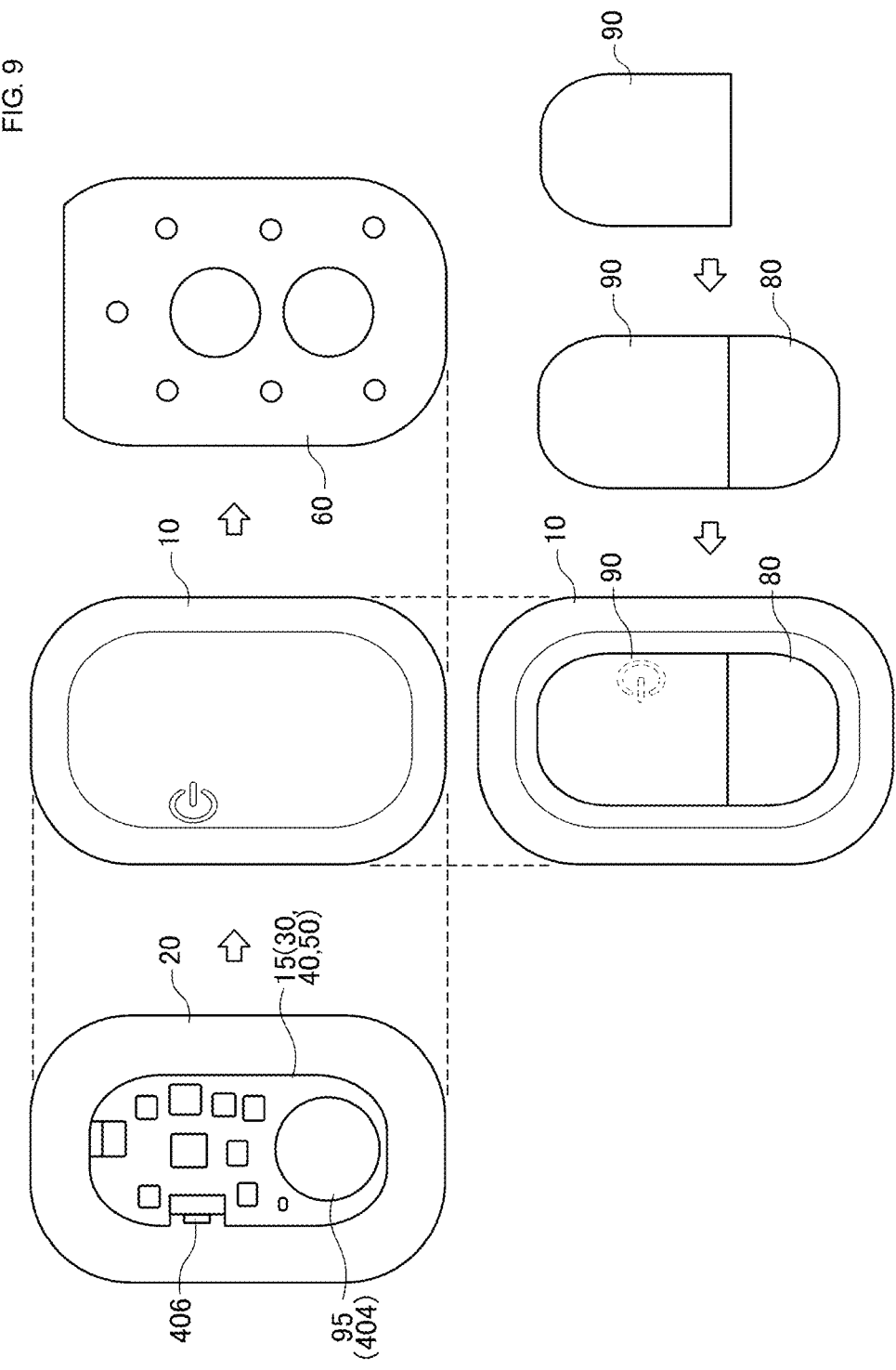
FIG. 9 is a view (part 2) for explaining the method of assembling the deep body thermometer according to the first exemplary embodiment.

Next, a method of assembling the deep body thermometer 1 (e.g., a manufacturing method) will be described with reference to FIG. 8 and FIG. 9. FIG. 8 is a view (part 1) for explaining the method of assembling the deep body thermometer 1. FIG. 9 is a view (part 2) for explaining the method of assembling the deep body thermometer 1.

The deep body thermometer 1 is assembled in the following steps (1) to (6), for example.

One surface of the thermal resistor layer 30 (i.e., the first thermal resistor 301 and the second thermal resistor 302) is fixed to the back surface of the wiring substrate 40 in a close contact manner by a double-sided adhesive tape.

After the flexible substrate 50 is connected to the FPC connector 407 of the wiring substrate 40, the flexible substrate 50 is fixed to the other surface of the thermal resistor layer 30 (i.e., the first thermal resistor 301 and the second thermal resistor 302) in a close contact configuration by a double-sided adhesive tape.

The coin battery 404 is fitted to the wiring board 40 (i.e., inserted into the battery holder 95 mounted on the wiring substrate 40).

The body temperature measuring unit 15 (i.e., the wiring substrate 40, the thermal resistor layer 30, the flexible substrate 50) on the flexible substrate 50 side is fixed to a central portion of the lower exterior body 20 in a close contact manner by a double-sided adhesive tape.

One surface of the lining member 80 is stuck to the back surface (i.e., rear surface) of the upper exterior body 10 by a double-sided adhesive tape, and the buffer member 90 is stuck to the other surface of the lining member 80 by a double-sided adhesive tape.

A peripheral edge portion of the upper exterior body 10 to which the lining member 80 and the buffer member 90 have been stuck and a peripheral edge portion of the lower exterior body 20 to which the body temperature measuring unit 15 has been fixed are fixed to each other in a close contact manner by a double-sided adhesive tape.

The sticking member 60 is stuck to the bottom surface of the lower exterior body 20. In this manner, the deep body thermometer 1 is assembled (e.g., manufactured). Note that, in the embodiment, since the first temperature sensor 701 and the third temperature sensor 703 are not arranged at symmetrical positions with respect to the center of the lower exterior body 20, a mark 20a for indicating the sticking direction of the sticking member 60 is put on the lower exterior body 20. The first temperature sensor 701 and the third temperature sensor 703 may be arranged at the symmetrical positions with respect to the center of the lower exterior body 20 and the mark 20a indicating the sticking direction of the sticking member 60 may be eliminated.

When the deep body thermometer 1 assembled as described above is used, first, a separator (e.g., a release paper) attached to the second adhesive layer 602 (e.g., double-sided adhesive tape) of the sticking member 60 is peeled off. Then, after the power supply switch 406 is pressed from an outer side portion (e.g., the side) of the upper exterior body 10 to turn ON the power supply, the deep body thermometer 1 is stuck to a measurement site of the user. Note that, since the power supply switch 406 may be erroneously pressed during the measurement, it is preferable that an operation of turning ON/OFF the power supply be received by, for example, a long pressing operation of equal to or more than several seconds or by a plurality of pressing operations. When the operation is received, the LED 405 emits light in a predetermined light emission pattern to inform the user that the operation has been received. When the power supply is turned ON, the deep body temperature measurement, storage of the measurement data in the memory, and wireless data output are started. Note that, in a case where the deep body temperature is measured, a measurement site is preferably the chest, the armpit, the back, the waist, the neck, back of the head, or the forehead, however, in a case where body temperature fluctuation is measured, the measurement site may be the abdomen, the flank, the thigh, the ankle, the arm, the wrist, or the like.

As described in detail above, according to the embodiment, since the power supply switch 406 is arranged on the side surface of the upper exterior body 10, the power supply switch 406 receives the operation input in which the input direction of the operation force is substantially parallel (i.e., from the side) with respect to the sticking member 60 (i.e., the body surface when the deep body thermometer 1 is stuck to the living body), and does not receive the operation input in which the input direction of the operation force is substantially perpendicular (i.e., from above) with respect to the sticking member 60. Therefore, even when force in a direction substantially perpendicular to the body surface is input to the power supply switch 406, the operation is not received. As a result, this configuration prevents the power supply switch 406 from being erroneously operated (i.e., receiving an erroneous switch operation).

Further, according to the embodiment, the upper exterior body 10 is made of the foamed material of closed cells or semi-closed cells having waterproof properties and is formed in a substantially hat-like shape in a side view, the sticking member 60 is stuck to an outer side surface of the lower exterior body 20, and the wiring substrate 40 is housed in an accommodation space defined by the upper exterior body 10 and the lower exterior body 20. Therefore, it is possible to press the power supply switch 406 from the outer side of the upper exterior body 10.

Moreover, according to the embodiment, since the power supply switch 406 is disposed inside (i.e., in the accommodation space of) the upper exterior body 10 so as not to make contact with the back surface of the side surface portion of the upper exterior body 10, it is possible to more reliably prevent the power supply switch 406 from being erroneously pressed (receiving the operation).

Second Exemplary Embodiment

Figure 10:
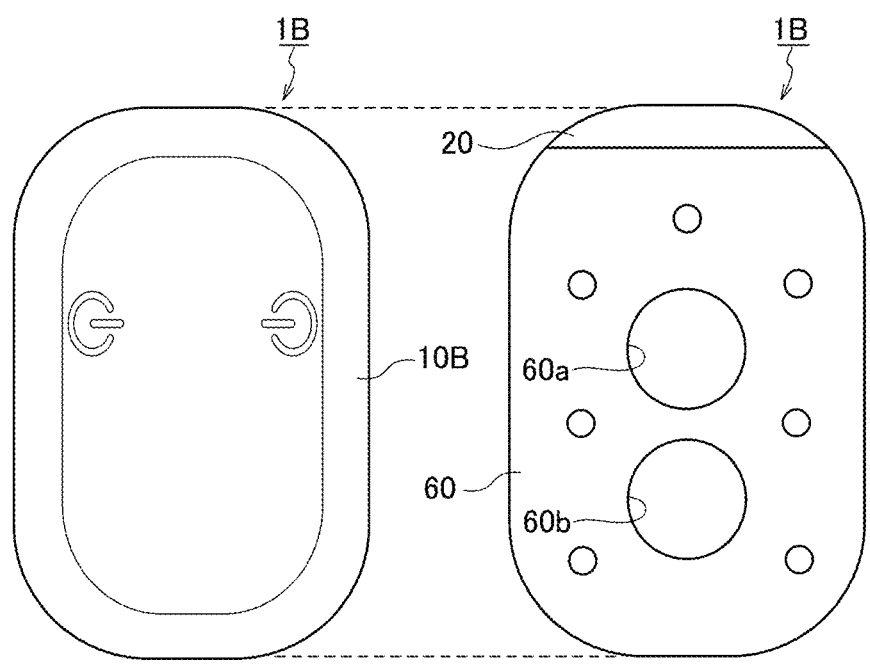
FIG. 10 includes a plan view and a bottom view illustrating an appearance of a deep body thermometer according to a second exemplary embodiment.
Figure 11:
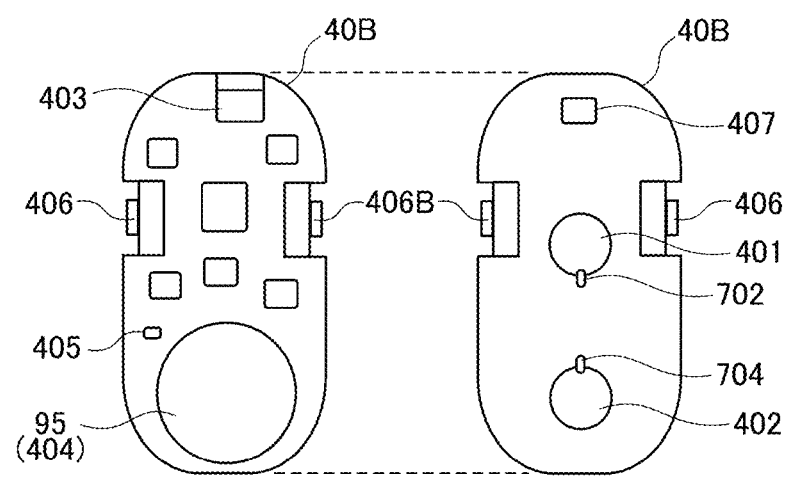
FIG. 11 includes a plan view and a bottom view illustrating a wiring substrate configuring the deep body thermometer according to the second exemplary embodiment.

Next, a deep body thermometer 1B according to a second embodiment will be described with reference to FIG. 10 and FIG. 11 together. Here, it is noted that the description of the same or similar configurations as or to those in the above-described first embodiment will be simplified or omitted, and different points are mainly described. FIG. 10 includes a plan view and a bottom view illustrating an appearance of the deep body thermometer 1B. FIG. 11 includes a plan view and a bottom view illustrating a wiring substrate 40B configuring the deep body thermometer 1B. Note that the same reference numerals are denoted to constituent elements which are the same as or equivalent to those in the first embodiment in FIG. 10 and FIG. 11.

The deep body thermometer 1B is different from the deep body thermometer 1 described above in that a plurality of operation switches 406 and 406B (e.g., two in this embodiment) that receive an operation by a user are provided.

The operation switch 406 and the operation switch 406B which receive an operation such as ON/OFF of a power supply by the user via an upper exterior body 10B are electrically connected to the wiring substrate 40B. A pair of notch portions is formed in opposing side portions of the wiring substrate 40B, and two operation switches 406 and 406B are attached so as to be housed in the respective notch portions (i.e., in a manner such that the operation switch 406 is housed in one notch portion and the operation switch 406B is housed in another notch portion) and in a manner such that a main surface of the wiring substrate 40B and respective operation directions of the operation switches 406 and 406B are substantially parallel to each other. The wiring substrate 40B is housed in an accommodation space defined by the upper exterior body 10B and the lower exterior body 20 such that each of the operation switch 406 and the operation switch 406B faces the back surface (i.e., rear surface) of the opposing side surface portions of the upper exterior body 10B. Note that positions of the notch portions do not necessarily need to be symmetrical, and may be shifted.

That is, the operation switch 406 and the operation switch 406B each are arranged on side surfaces of the upper exterior body 10B which are opposed each other. Note that each of the two operation switches 406 and 406B may be arranged on side surfaces which intersect each other, instead of the different side surfaces of the upper exterior body 10B, that is, the side surfaces which are opposed face each other. Further, for example, when the one operation switch 406 is arranged on the side surface of the upper exterior 10B, the other operation switch 406B may be arranged on a top surface of the upper exterior 10B. That is, it is only required that the operation switches 406 and 406B are arranged so as not to be turned on at the same time by one operation.

Therefore, the operation switch 406 and the operation switch 406B each receive an operation input in which an input direction (e.g., an operation direction) of operation force is substantially parallel (i.e., from the side of the upper exterior body 10B) with respect to the wiring substrate 40B and the sticking member 60 (i.e., the body surface when the deep body thermometer 1 is stuck to the living body), and do not receive an operation input in which an input direction (e.g., an operation direction) of operation force is substantially perpendicular (i.e., from above) with respect to the wiring substrate 40B and the sticking member 60. Note that, as described above, a configuration can be provided in which only one of the operation switch 406 and the operation switch 406B receives only the operation input in which the input direction (e.g., an operation direction) of the operation force is substantially parallel (i.e., from the side of the upper exterior body 10B) with respect to the wiring substrate 40B.

It is also noted that as described above, as the operation switches 406 and 406B, for example, a push button switch, a rocker switch, or the like is preferably used. Additionally, in a case of the push button switch, a push button switch employing an alternate operation of holding an ON state even when a fingertip is separated therefrom is preferably used. Further, the operation switches 406 and 406B are preferably a surface mount type, but a lead type may also be used. However, the operation switch 406 and the operation switch 406B do not need to be of the same type, and may be of different types.

Moreover, similarly to the above-described first embodiment, in order to prevent the operation switches 406 and 406B from being erroneously (e.g., accidentally) pressed down and prevent the operation switches 406 and 406B from pushing up the upper exterior body 10B, each of the operation switches 406 and 406B is disposed inside (in the accommodation space of) the upper exterior body 10B so as not to make contact with the back surface of the side surface portion of the upper exterior body 10B.

In the embodiment, the operation is received in accordance with a combination of a plurality of operation inputs input to each of the two operation switches 406 and 406B, respectively. In this case, the operation is received in further consideration of operation timing of each of the two operation switches 406 and 406B. In this way, for example, the following functions (1) to (4) can be added according to an exemplary aspect.

A function of receiving an operation only in a case where each of the two operation switches 406 and 406B is operated at the same time.

A function of enabling an operation in a case where one operation switch 406 is operated first and then the other operation switch 406B is operated.

A function of enabling an operation in a case where the one operation switch 406 is operated for, for example, equal to or more than one second, and then the other operation switch 406B is operated for, for example, equal to or more than two seconds.

A function of shifting (e.g., switching) a mode in a case where the two operation switches 406 and 406B are simultaneously operated in turning ON/OFF of the power supply, and the operation switch 406 or the operation switch 406B is operated in the ON state of the power supply. Note that, examples of the mode include a short-time measurement mode in which measurement is performed in a short time, a memory mode (e.g., a recording mode) in which measurement data is stored in an internal memory, a sleep mode, and the like. Further, a mode in which the deep body temperature is measured, a mode in which measurement of an electrocardiogram or the like is performed in addition to the deep body temperature, and the like are also exemplified.

It is noted that the other configurations are the same as or similar to those of the deep body thermometer 1 according to the first embodiment described above, and thus detailed description thereof will be omitted here.

According to the embodiment, two operation switches 406 and 406B that receive an operation by a user are provided, and each of the two operation switches 406 and 406B receives the operation input in which the operation direction is substantially parallel (i.e., from the side) with respect to the wiring substrate 40B and the sticking member 60 (that is, the body surface when the deep body thermometer 1 is stuck to the living body), and does not receive the operation input in which the operation direction is substantially perpendicular (i.e., from above) with respect to the sticking member 60. Therefore, even when the force in the direction substantially perpendicular to the body surface is input to the operation switch 406, the operation is not received. As a result, it is possible to more reliably prevent the operation switch 406 from being erroneously operated (i.e., receiving an erroneous switch operation).

In particular, according to the embodiment, since the respective two operation switches 406 and 406B are arranged on different side surfaces of the upper exterior body 10B (the side surfaces opposed each other in the embodiment), it is possible to prevent the operation switch 406 from being erroneously operated more effectively (i.e., receiving an erroneous switch operation).

Further, according to the embodiment, the operation is received in accordance with the combination of operation inputs input to each of the two operation switches 406 and 406B, and the operation timing of each of the two operation switches 406 and 406B. Therefore, it is possible to add the above-described various functions while an erroneous operation is reliably prevented.

It is noted that while the exemplary embodiments have been described above, the invention is not limited to the embodiments described above, and various variations can be made. For example, in the above embodiments, the exemplary embodiments are provided for the two-heat flux-type deep body thermometer as the example for description, but the exemplary embodiments can be provided for a one-heat flux-type deep body thermometer. In addition, the exemplary thermometer can be provided for other than the deep body thermometer. For example, the exemplary embodiments can also be provided for an electrocardiograph and a sticking-type device for a living body, which measures respiration and pulses, and the like, for example.

In an exemplary aspect, the operation switch 406 (406B) may be arranged on another side surface of the upper exterior body 10 (10B), while the arrangement thereof is not limited to the above-described embodiments. Further, the upper exterior body 10 (10B), which has a substantially hat shape, may have a substantially trapezoidal shape.

In the embodiments described above, the operation switch 406 is attached so as to be orthogonal to the wiring substrate 40 (the sticking member 60), however, the operation switch 406 may be attached in parallel to the wiring substrate 40 (the sticking member 60), and the input direction may be converted by using a link mechanism which converts the direction of the operation force. That is, a configuration may also be adopted in which the operation input (from the side) in a parallel direction is converted into an operation input (from above) in a vertical direction via the link mechanism to press the operation switch 406.

It is also noted that the shapes, sizes, and arrangement of each of the thermal resistor layer 30 (the first thermal resistor 301 and the second thermal resistor 302), the wiring substrate 40, the flexible substrate 50, the lining member 80, the buffer member 90 described above and the arrangement and the like of the first temperature sensor 701 to the fourth temperature sensor 704 are not limited to those in the above embodiments, and can be desirably set in accordance with requirements such as accuracy, for example.

REFERENCE SIGNS LIST 1, 1B DEEP BODY THERMOMETER (STICKING-TYPE DEVICE FOR LIVING BODY)
10, 10B UPPER EXTERIOR BODY
15 BODY TEMPERATURE MEASURING UNIT
20 LOWER EXTERIOR BODY
30 THERMAL RESISTOR LAYER
301 FIRST THERMAL RESISTOR
302 SECOND THERMAL RESISTOR
301a, 302a THROUGH-HOLE
40, 40B WIRING SUBSTRATE
401, 402 THERMAL EQUALIZATION PATTERN
403 WIRELESS COMMUNICATION UNIT
404 COIN BATTERY
405 LED
406, 406B OPERATION SWITCH/POWER SUPPLY SWITCH
407 FPC CONNECTOR
50 FLEXIBLE SUBSTRATE
501, 502 THERMAL EQUALIZATION PATTERN
60 STICKING MEMBER
601 FIRST ADHESIVE LAYER
602 SECOND ADHESIVE LAYER
603 VENTILATION LAYER
60a, 60b THROUGH-HOLE
701, 702, 703, 704 TEMPERATURE SENSOR
80 LINING MEMBER
90 BUFFER MEMBER
95 BATTERY HOLDER

The invention claimed is:

1. A device configured to adhere to a living body, the device comprising:
   an exterior body having an accommodation space therein;
   a sticking member having adhesiveness with a first surface stuck to a bottom surface of the exterior body;
   a wiring substrate housed in the accommodation space and including a notch in a side portion thereof; and
   an operation switch electrically connected to the wiring substrate and housed in the notch in the side portion of the wiring substrate so as to face at least one side surface of the exterior body,
   wherein the operation switch is arranged in the accommodation space of the exterior body to fit entirely within the notch and is structurally configured to be spaced apart from the at least one side surface of the exterior body, and
   wherein the operation switch is constructed to receive an operation input having an input direction of operation force being substantially parallel to a main surface of the sticking member, such that the operation switch is constructed to not receive the operation input with the input direction of operation force being substantially perpendicular to the main surface of the sticking member.

2. The device according to claim 1, wherein the operation switch is arranged so as to not make contact with a back surface of the exterior body.

3. The device according to claim 1, wherein the exterior body has a top surface, the bottom surface, and the at least one side surface that connects the top surface and the bottom surface.

4. The device according to claim 1, wherein the operation switch is a push-button switch for an alternate operation.

5. The device according to claim 1, wherein the exterior body comprises a foamed material of closed cells or semi-closed cells having waterproof properties.

6. The device according to claim 5, wherein the exterior body comprises:
   an upper exterior body comprising a substantially hat-like shape or a substantially trapezoidal shape in a side view; and
   a lower exterior body having a peripheral edge that is in close contact with the upper exterior body,
   wherein the first surface of the sticking member is adhered to an outer side surface of the lower exterior body, and
   wherein the accommodation space is defined by the upper exterior body and the lower exterior body.

7. The device according to claim 1, further comprising a biological sensor configured to detect a biological signal from the living body that is electrically connected to the wiring substrate.

8. The device according to claim 7, wherein the biological sensor is a temperature sensor configured to detect a temperature of a living body.

9. The device according to claim 1, wherein the operation switch comprises a plurality of operation switches configured to receive a plurality of operation inputs performed by a user, with the plurality of operation switches housed in respective notches in the side portion of the wiring substrate.

10. The device according to claim 9, wherein at least one of the plurality of operation switches is positioned to receive the operation input having an operation direction substantially parallel to the main surface of the sticking member, such that the at least one operation switch does not receive the operation input having the operation direction being substantially perpendicular to the main surface of the sticking member.

11. The device according to claim 10, wherein the plurality of operation inputs are configured to receive a combination of inputs.

12. The device according to claim 11, wherein respective operation inputs of the plurality of operation inputs are received based on an operation timing of each of the plurality of operation switches.

13. The device according to claim 10, wherein the exterior body has a plurality of side surfaces including the at least one side surface, and each of the plurality of operation switches is disposed on a different side surface of the plurality of side surfaces of the exterior body.

14. The device according to claim 13, wherein each of the plurality of operation switches is disposed on a respective side surface of the plurality of side surfaces that oppose each other.

15. The device according to claim 13, wherein each of the plurality of operation switches is disposed on a different side surface of the plurality of side surfaces and a top surface of the exterior body.

16. A device that adheres to a living body, the device comprising:
- an exterior body having an accommodation space therein;
- a sticking member having an adhesive layer coupled to a bottom surface of the exterior body;
- a wiring substrate housed in the accommodation space and including a notch in a side portion thereof; and
- an operation switch electrically connected to the wiring substrate and housed in the notch in the side portion of the wiring substrate so as to face at least one side surface of the exterior body,
- wherein the operation switch is arranged in the accommodation space of the exterior body to fit entirely within the notch and is structurally configured to be spaced apart from the at least one side surface of the exterior body, and
- wherein the operation switch is positioned within the accommodation space to receive an operation input in an input direction that is substantially parallel to a main surface of the sticking member.

17. The device according to claim 16, wherein the operation switch is structurally positioned within the accommodation space such that the operation switch cannot receive the operation input at an input direction that is substantially perpendicular to the main surface of the sticking member.

18. The device according to claim 16, wherein the operation switch is arranged so as to not make contact with a back surface of the exterior body.

19. The device according to claim 16,
- wherein the exterior body comprises a foamed material of closed cells or semi-closed cells having waterproof properties,
- wherein the exterior body comprises:
  - an upper exterior body having a substantially hat-like shape or a substantially trapezoidal shape in a side view thereof, and
  - a lower exterior body having a peripheral edge that is coupled to the upper exterior body to define the accommodation space of the exterior body, and
- wherein the adhesive layer of the sticking member is adhered to an outer side surface of the lower exterior body.

20. The device according to claim 16, wherein the operation switch is a push-button switch.

* * * * *